United States Patent
Epstein et al.

(10) Patent No.: US 8,326,389 B2
(45) Date of Patent: Dec. 4, 2012

(54) SYSTEM FOR IN VIVO BIOSENSING BASED ON THE OPTICAL RESPONSE OF ELECTRONIC POLYMERS

(75) Inventors: Arthur J. Epstein, Bexley, OH (US); Louis R. Nemzer, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 698 days.

(21) Appl. No.: 12/517,966

(22) PCT Filed: Dec. 5, 2007

(86) PCT No.: PCT/US2007/025044
§ 371 (c)(1),
(2), (4) Date: Jul. 17, 2009

(87) PCT Pub. No.: WO2008/143651
PCT Pub. Date: Nov. 27, 2008

(65) Prior Publication Data
US 2010/0324383 A1    Dec. 23, 2010

Related U.S. Application Data

(60) Provisional application No. 60/873,466, filed on Dec. 7, 2006.

(51) Int. Cl.
*A61B 5/1455* (2006.01)
(52) U.S. Cl. .......................... 600/310; 600/316; 600/322
(58) Field of Classification Search .................. 600/310, 600/316, 322, 326, 327, 473, 476; 435/4, 435/14, 26, 128, 174, 183; 525/183, 207, 525/327.6, 540; 422/50, 82.05, 82.06
See application file for complete search history.

(56) References Cited

U.S. PATENT DOCUMENTS

| | | | |
|---|---|---|---|
| 4,458,686 A * | 7/1984 | Clark, Jr. ...................... | 600/358 |
| 5,032,506 A * | 7/1991 | Palmer et al. .................... | 435/26 |
| 5,159,031 A | 10/1992 | Epstein et al. | |
| 5,164,465 A * | 11/1992 | Epstein et al. ................ | 525/540 |

(Continued)

FOREIGN PATENT DOCUMENTS
WO    01/26708 A1    4/2001

OTHER PUBLICATIONS

Tohda, K. et al., A Microscopic, Continuous, Optical Monitor for Interstitial Electrolytes and Glucose, Chemphyschem 2003, 4, pp. 155-160.
Bossi et al., Towards the development of an integrated capillary electrophoresis optical biosensor, Electrophoresis 2003, 24, pp. 3356-3363.

(Continued)

*Primary Examiner* — Eric Winakur
*Assistant Examiner* — Chu Chuan Liu
(74) *Attorney, Agent, or Firm* — MacMillan, Sobanski & Todd, LLC

(57) ABSTRACT

A system for continuous in vivo biosensing of specific analyte molecule concentrations based on the dynamic optical properties of electronic polymers is disclosed. The biosensor system includes at least one implant member subcutaneously exposed to the interstitial fluid of the subject, and a reader member at least temporarily positioned over the implant member to probe it with light of specific wavelengths through the skin. The system has many potential applications, including the real-time monitoring of blood glucose levels in diabetics as a method to supplement or replace conventional capillary blood testing.

31 Claims, 6 Drawing Sheets

U.S. PATENT DOCUMENTS

| | | | |
|---|---|---|---|
| 5,352,574 A * | 10/1994 | Guiseppi-Elie | 435/4 |
| 5,451,526 A | 9/1995 | Cui et al. | |
| 5,920,393 A * | 7/1999 | Kaplan | 356/364 |
| 6,002,954 A | 12/1999 | Van Antwerp et al. | |
| 6,043,878 A | 3/2000 | Gratzl et al. | |
| 6,049,727 A * | 4/2000 | Crothall | 600/310 |
| 6,574,490 B2 * | 6/2003 | Abbink et al. | 600/316 |
| 6,804,544 B2 | 10/2004 | Van Antwerp et al. | |
| 2001/0030325 A1 | 10/2001 | Epstein et al. | |
| 2002/0177637 A1 | 11/2002 | Epstein et al. | |
| 2003/0001154 A1 | 1/2003 | Epstein et al. | |
| 2003/0022020 A1 | 1/2003 | Epstein et al. | |
| 2003/0022409 A1 | 1/2003 | Epstein et al. | |
| 2003/0171666 A1 | 9/2003 | Loeb et al. | |
| 2004/0043251 A1 | 3/2004 | Epstein et al. | |
| 2004/0109350 A1 | 6/2004 | Epstein | |
| 2004/0180391 A1 | 9/2004 | Gratzl et al. | |
| 2005/0027097 A1 | 2/2005 | Epstein et al. | |
| 2005/0187375 A1 | 8/2005 | Epstein et al. | |
| 2005/0221276 A1 | 10/2005 | Rozakis et al. | |
| 2006/0057743 A1 | 3/2006 | Epstein et al. | |
| 2006/0240324 A1 | 10/2006 | Epstein et al. | |
| 2006/0291142 A1 | 12/2006 | Grigorian et al. | |
| 2007/0034836 A1 | 2/2007 | Epstein et al. | |

OTHER PUBLICATIONS

Tohda et al., Micro-miniature Autonomous Optical Sensor Array for Monitoring Ions and Metabolites 1: Design, Fabrication, and Data Analysis, Analytical Sciences, Mar. 2006, vol. 22, pp. 383-388.

Tohda et al., Micro-miniature Autonomous Optical Sensor Array for Monitoring Ions and Metabolites 2: Color Responses to pH, K+ and Glucose, Analytical Sciences, Jul. 2006, vol. 22, pp. 937-941.

PCT International Search Report-Opinion dated Oct. 28, 2008, PCT/US2007/025044, Dec. 5, 2007.

PCT International Preliminary Report on Patentability dated Jun. 18, 2009, PCT/US2007/025044, Dec. 5, 2007.

European Search Report Communication, Application No. 07874163.4, Date Sep. 22, 2011.

European Examination Report, Application No. 07874163.4 dated Jun. 21, 2012.

Pringsheim, E. et al., "Optical Sensing of pH Using Thin Films of Substituted Polyanilines," Analytica Chimica Acta, Dec. 1997, pp. 247-252, vol. 357, Issue 3.

Xian, Y. et al., "Glucose Biosensor Based on Au Nanoparticles-Conductive Polyaniline Nanocomposite," Biosensors and Bioelectronics, Apr. 2006, pp. 1996-2000, vol. 21, No. 10.

* cited by examiner

SYSTEM FOR IN VIVO BIOSENSING BASED ON THE OPTICAL RESPONSE OF ELECTRONIC POLYMERS

CROSS-REFERENCE TO RELATED APPLICATIONS and STATEMENT REGARDING FEDERALLY SPONSORED RESEARCH This application claims the benefit of U.S. Provisional Application No. 60/873,466, filed Dec. 7, 2006, the disclosure of which is incorporated herein by reference. This invention was made with no Government support and the Government has no rights in this invention.

TECHNICAL FIELD AND INDUSTRIAL APPLICABILITY OF THE INVENTION

This invention is directed to a system for in vivo biosensing of analyte molecule concentrations based on the optical properties of a polymer in a subject. The biosensor system includes at least one implant member subcutaneously positioned under skin in the subject and exposed to interstitial fluid of the subject and at least one reader at least temporarily positioned to send and receive.

BACKGROUND OF THE INVENTION

A biosensor is a device that employs a biological sensing element to produce an electrical or optical signal in proportion to the concentration of a particular substance of interest, often referred to as the analyte. In order for a biosensor to operate, it must make use of a chemical reaction or measurable property change. Since many medical conditions are diagnosed or monitored by measuring the concentration of certain characteristic analytes, modern medicine relies heavily on biosensors to accurately direct the course of treatment.

In vivo optical biosensors, which operate based on changes in the absorbance and/or reflectance of certain diagnostic wavelengths of light incident on some part of the patient, can offer high accuracy while being much less invasive than alternative methods that require a sample to be taken, or that utilize electrodes which penetrate the skin.

For example, the pulse oximeter is a widely-used, highly reliable, and minimally invasive in vivo optical biosensor. Pulse oximetry is most often used to monitor blood oxygenation levels by shining light through a fingertip and calculating the ratio of the absorbance of light at 660 and 910 nm by the bloodstream. Oxygenated and deoxygenated hemoglobin absorb differently near 660 nm. Specifically, oxygenated hemoglobin is red, which means it weakly absorbs red light. In contrast, deoxygenated hemoglobin absorbs strongly at 660 nm, giving it a blue color. Both states absorb similarly at 910 nm, so the ratio of absorbance values can be used to find the percentage of hemoglobin molecules that are oxygenated. However, in vivo optical biosensing has, to this point, generally been limited to biomolecules, like hemoglobin, that happen to have discernable optical features within the "optical window" of light wavelengths that can pass through the skin without being overly absorbed or scattered. Because of this interference, primarily caused by the water content of living tissue, as well as other confounding species that may absorb at nearby wavelengths, many important analytes, including glucose, have resisted attempts to be detected through minimally invasive, in vivo optical biosensors.

Glucose monitoring itself is extremely important in the course of treatment for diabetes mellitus. Diabetes is a widespread, chronic condition with significant public health implications. In particular, this metabolic disorder can lead to severe medical complications and consumes a large amount of health care resources every year. According to the American Diabetes Association, there are an estimated 20.8 million diabetics in the United States, representing 7% of the population, with this number only expected to increase in the future. The total annual economic cost in 2002 was estimated to be $132 billion, including $92 billion in direct medical costs and another $40 billion for indirect costs attributed to disability, work absenteeism, and premature mortality. Complications of diabetes can include: heart disease, stroke, high blood pressure, blindness, kidney disease, nervous system damage, amputations, dental disease, and sexual dysfunction. Essential to preventing these complications is a treatment regimen that maintains blood glucose concentrations within normal limits. However, the current solution of "fingerstick" testing of the blood glucose from capillary blood four or five times a day to calibrate insulin injections is a significant burden on patients. The pain and inconvenience of testing reduces compliance and can lead to inadequate control of blood sugar levels. Additionally, dangerous spikes or dips in blood sugar between tests may go unnoticed, and levels are unknown during times when testing is not feasible, such as when the patient is sleeping.

Thus, there remains a need for a continuous monitoring system that can display and record glucose levels in real time, sound visual and/or audible alarms during hyper- or hypoglycemic events, and work in a feedback loop with an insulin pump. Although significant progress has been made in improving commercial realtime implantable monitors, for example, systems that use data collected amperometrically from implanted electrodes, many barriers still remain that prevent them from enjoying more widespread use. Considerations of cost, reliability, invasiveness, and lifetime justify a continued search for alternative continuous sensing methods. Since glucose lacks significant optical absorptions in the range of wavelengths skin is transparent to, attempts directly measure it through in situ optical techniques have been difficult.

Considering the above-mentioned concerns, there is a need for a system capable of in vivo biosensing that will provide a high level of patient compliance.

In particular, it is clear that there remains a need in the art for an improved system to aid in the effective treatment of such diseases as diabetes.

SUMMARY OF THE INVENTION

In a broad aspect, there is provided a system for in vivo biosensing of specific analyte molecule concentrations based on dynamic optical properties of a polymer in a subject. The biosensor system includes at least one implant member subcutaneously positioned under skin in the subject and exposed to interstitial fluid of the subject. The implant member includes a reflective substrate having deposited thereon at least one polymer and at least one sensitizing agent that causes an oxidation-reduction reaction with the polymer in the presence of the target analyte molecule. The biosensor system also includes at least one reader member that is at least temporarily positioned adjacent to the implant member. The reader member probes the implant member with light having one or more specific wavelengths, and detects a reflected signal from the implant member. The biosensor system also includes at least one data system that is used to determine a concentration of the target analyte molecule.

In another broad aspect, there is provided herein a method for in vivo biosensing of specific analyte molecule concentrations based on dynamic optical properties of a polymer. The method includes subcutaneously positioning at least one implant member in a subject wherein the implant member is exposed to interstitial fluid of the subject. The method also includes at least temporarily positioning a reader member adjacent to the implant member. The reader member probes the implant member with light of specific wavelengths through the skin and detects a reflected signal from the implant member.

The method also includes calculating the analyte concentration and relaying information about the analyte concentration to a display, computer, and/or treatment device. In certain embodiments, the method further includes substantially continuously detecting the reflected signal from the implant member.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
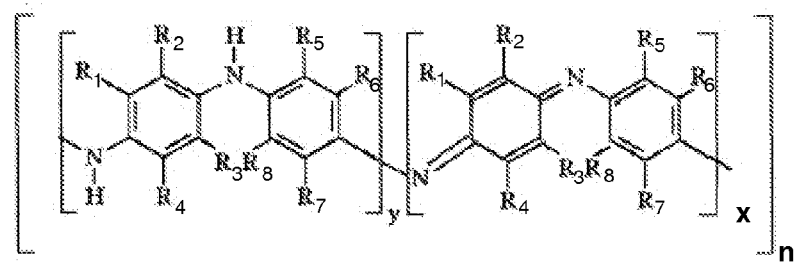
FIG. 1 shows the chemical structure of Polyaniline.

In a broad aspect, there is provided herein a system that allows for the in situ detection of a wide range of analytes by sensing the optical changes of a specially sensitized biocompatible implant, rather than optical changes due to the analyte directly. In a particular embodiment, the system includes an implant that is designed to change its reflective properties at diagnostic light wavelengths to which human skin is generally transparent. The implant can be easily probed with light with the appropriate system of light sources, detectors, and electronics. It should be understood, in the system described herein, that polymer itself can be a functional, as well as a structural component, and not merely a support matrix as it is in some other devices.

In another broad aspect, there is provided herein a system for continuous in vivo clinical monitoring of certain biomolecules based on the dynamic optical response of electronic polymers in the presence of a specific immobilized enzyme or other sensitizing agent. The system includes a subcutaneous implant member (containing a polymer:sensitizing agent material; such as a thin film and/or fiber network material on a reflective substrate) that is exposed to the patient's interstitial fluid. A reader member is brought into proximity to the implant in order to read the level of material in the interstitial fluid being sensed, as further explained below.

In one embodiment, the ultraviolet-visible-near infrared (UV-VIS-NIR) absorbance and reflectance of the implant are modulated by variations in the oxidation state of the polymer, which is sensitive to oxidation-reduction reactions catalyzed by the enzyme dependent on the concentration of glucose. Then, the reader can probe the implant with light of specific diagnostic wavelengths through the skin and calculate the analyte concentration. For example, the system can be fabricated with glucose oxidase as the enzyme and used to display and record a patient's blood sugar level in real time. This semi-invasive device can be used by diabetic patients to reduce or eliminate the need for conventional fingerprick blood sugar testing.

In another broad aspect, by using a particular chosen sensitizing agent, the biosensor can also be used to detect other biologically relevant analyte concentrations.

In one particular embodiment, the polymer component useful in the polymer:sensitizing agent material can be an electronic polymer that has an optical absorption spectrum in the UV-VIS-NIR range that is dependent on the polymer's oxidation state. In a particular embodiment, the electronic polymer can be a polyaniline material.

Electric polymers, also known as "conducting" or "conjugated" polymers, such as polyaniline (a synthetic organic electronic polymer), have desirable properties, including a range of electrical conductivity that spans up to ten orders of magnitude, depending on oxidation state, proton doping, and exact method of preparation. The oxidation state also affects the polymer's optical absorption spectrum, and the oxidation state can be determined based on its UV-VIS spectrum. Polyaniline is also biocompatible, which increases the implant's functional lifetime.

In a particular embodiment, the enzyme component useful in the polymer:sensitizing agent material can be an oxidase material. In one embodiment, a particularly suitable enzyme component can comprise glucose oxidase (GOx) which is a naturally occurring enzyme harvested from the fungus *Aspergillus niger* that catalyzes the oxidation of glucose with very high specificity. In such embodiment, a concentration of glucose in the presence of the GOx is established. The presence of GOx affects the oxidation state of Polyaniline material such that there is a real-time reading of the glucose levels in the interstitial fluid. Thus, the biosensor device can determine the glucose concentration based on optical absorption/reflection data.

The optical absorption spectrum of the conducting polymer polyaniline in the UV-VIS-NIR range is dependent on the polymer's oxidation state and level of protonation. This is due to the increased conjugation of the pi-bonds in the polymer backbone when some of the amine repeat units, which have two benzenoid rings and are denoted by the index y, are oxidized to imine groups with one benzenoid ring and one quiniod ring and are denoted by the index x. The sum of x plus y is equal to 1 for polyaniline.

When y=1 (x=0) and all of the repeat units are amine, polyaniline is in its completely reduced state, known as leucoemeraldine base (LEB). At the other extreme, the completely oxidized state, pernigraniline (PB) occurs when y=0 (x=1) and all of the repeats are imine. The intermediate oxidation state of y=0.35-0.65 (x=0.65-0.35) is referred to as emeraldine base (EB).

As FIG. 1 indicates, the polymer chain can be functionalized with side R-groups (groups shown as $R_1$, $R_2$, $R_3$, and $R_4$ independently bonded to one of the 4 carbon atoms in the benenoid or quinoid $C_6$ ring not bound to a N in order to modify the polyaniline properties and/or improve processing. The $R_1$ through $R_8$ are independently selected from the group consisting of —H, —OCH$_3$, —CH$_3$, —F, —Cl, —Br, —I, —NR'$_2$, —NHCOR', —OH, —O, —SR', —OR', —OR', —OCOR', —NO$_2$, —COOH, —COOR', —COR', —CHO, and —CN, where R' is a $C_1$ to $C_{12}$ alkyl, aryl, or aralalkyl group. For example, the substitution groups can be chosen so that the polymer's absorption spectrum peaks at a wavelength that passes more readily through human skin. This ability to "tune" the polymer's properties using organic chemistry provides a primary advantage as compared with methods utilizing purely inorganic components.

Figure 2:
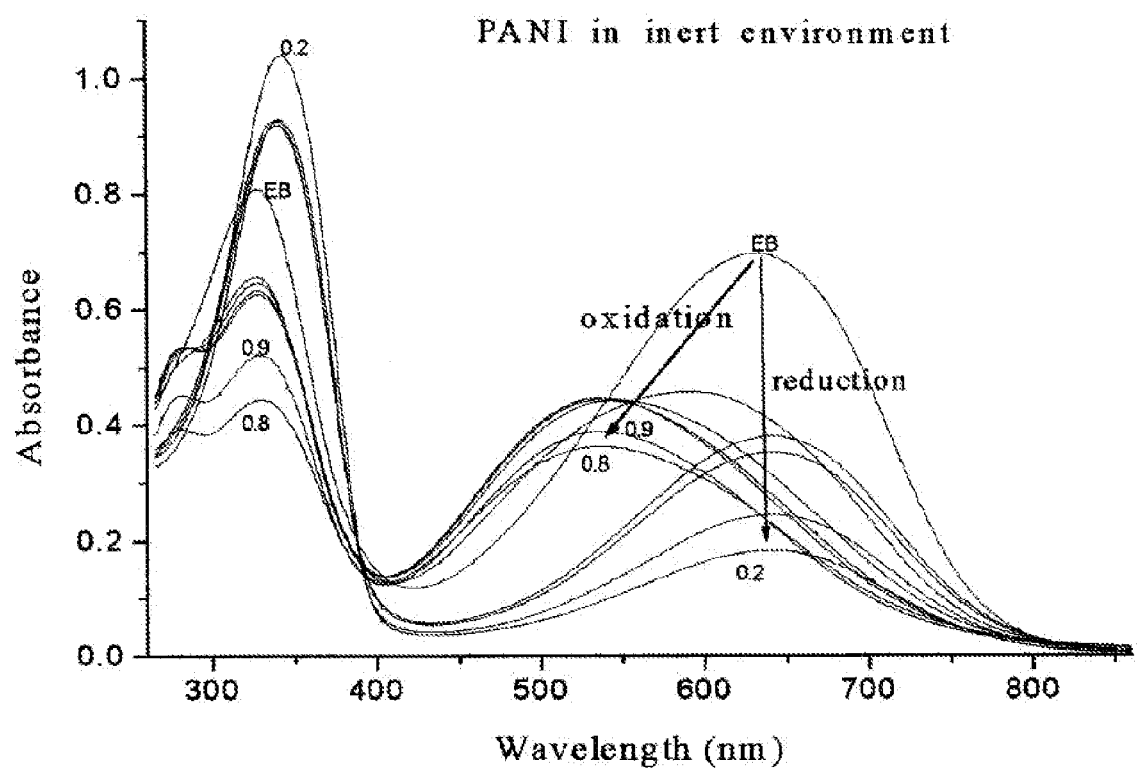
FIG. 2 is a graph showing the absorption spectra of polyaniline dissolved in NMP [Numbered Curved refer to x]. Samples of emeraldine base are reduced by calculated amounts of ascorbic acid or oxidized by ammonium peroxydisulfate.

Further, in certain embodiments, some of the polymer repeat units may also be replaced with repeats of other species. These "copolymers" offer additional flexibility when designing the device for optimal performance. In the LEB form, only a π-π* transition band is present in the UV-VIS spectrum, near 330 nm and an infrared peak at 1500 cm$^{-1}$. The half oxidized form, EB, and the fully oxidized form, PB, also have these transitions and additionally exhibit an absorptions in the range of 400-800 nm and at 1150 cm$^{-1}$ and 1590 cm$^{-1}$, but for different reasons. In EB, the peak near 650 nm is due to an exciton transition in which a valence electron from an amine repeat unit is excited to the LUMO level (conduction band) centered on an adjacent imine repeat unit. This leaves behind a hole which can then form a bound pair with the excited electron. This peak essentially disappears in the LEB form since there are very few or no imine repeats. In PB the peak at 540 nm is due to the "Peierls gap" as explained below. (See FIG. 2).

The half oxidized form, EB, and the fully oxidized form, PB, have an infrared absorption at 1500 cm$^{-1}$ present also in the LEB form. The half oxidized form, EB, and the fully oxidized form, PB, also have infrared absorptions at 1150 cm$^{-1}$ and 1590 cm$^{-1}$, neither present in the fully reduced LEB form. It is noted that the 1500 cm$^{-1}$ IR peak is associated with a vibrational mode of the amine (benenoid) ring while the 1590 cm$^{-1}$ is associated with a vibrational mode of an imine (quinoid ring), while the 1150 cm$^{-1}$ is associated with Raman active bands of the amine groups that are IR active in the EB and PB forms.

Figure 3:
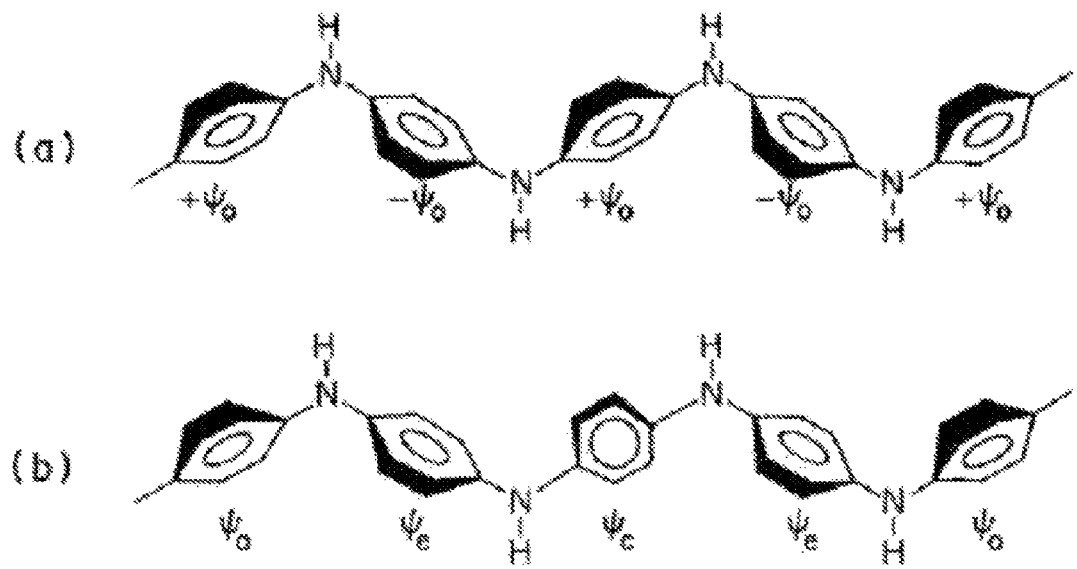
FIG. 3 shows the structure of (a) EB and (b) LEB with torsion angles shown.

The optical responses in the range of 400-800 nm can be understood by considering the conformational states that minimize the total energy of the polymer chain. When the polymer is drawn in the most realistic way, it becomes clear that the hydrogens on adjacent rings will experience steric repulsion. See, for example, FIG. 3 which shows the structure of (a) EB and (b) LEB with torsion angles shown.

This causes the rings to tilt out of the plane of the nitrogens. However, this effect of steric hindrance competes with the pi electron conjugation, which minimizes electronic energy when the nitrogen $p_z$ orbital is aligned with the ring pi-system. Therefore, the polymer will reach some equilibrium dihedral (torsion) angle. In the LEB form, where all of the rings are benzenoid, energy is minimized when the dihedral angles alternate as $+\psi_0, -\psi_0, +\psi_0, -\psi_0 \ldots$ where $\psi_0$ is approximately 56°.

In contrast, in the PB form, every other ring is quinoid and the carbon-nitrogen bonds in these rings are double bonds, not single bonds as in benzeniod rings. Therefore, there is a greater resistance to rotation, which leads to torsion angle dimerization similar to the Peierls transition seen in linear polymer chains such as polyacetylene. Peierls instability is an important feature of quasi-1D systems and occurs when a system can reduce its total energy by going from a state equally spaced atoms to one that forms dimers. The Peierls transition lowers the energy of the occupied states but raises the energy of the empty states. This creates the characteristic "Peierls gap" and also explains why these polymers are not conductive until doped. Here, the "dimers" take the form of torsion angle coordination, which manifests as angles that differ from simple alternation as $+\psi_0+\delta, -\psi_0+\delta$, where $\delta$ is the deviation from the LEB equilibrium torsion angle.

Figure 4:
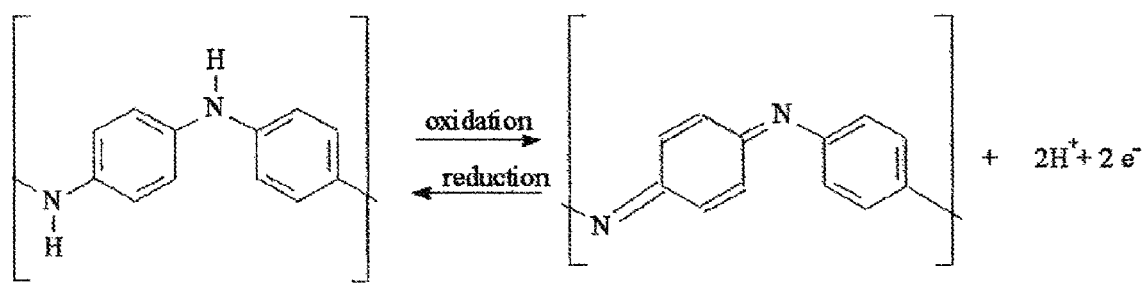
FIG. 4 shows the oxidation-reduction reaction that alters the form of polyaniline.

The difference in optical properties between the oxidation states can be detected by the unaided eye. EB in N-Methyl-2-pryrrolidone (NMP) solution or cast as a thin film and/or fiber network is blue to dark purple in color when viewed in transmission, while LEB is white to yellow. Polyaniline can be easily changed from one form to another in the presence of a suitable oxidizing or reducing agent. FIG. 4 shows that an amine group can be oxidized to an imine group through the abstraction of two protons and two electrons. In the reverse reaction, a reducing agent can donate two protons and two electrons to transmute an imine group to an amine. For example, EB can be reduced by ascorbic acid (vitamin C) to form LEB, which is unstable in the ambient air and is susceptible to being reoxidized by atmospheric oxygen. The reaction of controlled atmosphere $O_2$ with pristine LEB has been found to follow pseudo-first-order kinetics.

Glucose oxidase (GOx) is an enzyme that catalyzes the oxidation of β-D-glucose to D-glucono-1,5-lactone with $O_2$ as the electron and proton acceptor, creating hydrogen peroxide ($H_2O_2$) as a byproduct. D-glucono-1,5-lactone then spontaneously hydrolyzes to gluconic acid (D-Gluconate):

1. β-D-glucose+$O_2$→D-glucono-1,5-lactone+$H_2O_2$
2. D-glucono-1,5-lactone+OH$^-$→Gluconic Acid In the present system, glucose is covalently bonded or otherwise immobilized in the polymer matrix. Then, in the presence of glucose, polyaniline acts as the electron and proton recipient instead of oxygen:

1. β-D-glucose+EB→LEB+D-glucono-1,5-lactone
2. D-glucono-1,5-lactone+OH$^-$→Gluconic Acid.

Figure 5:
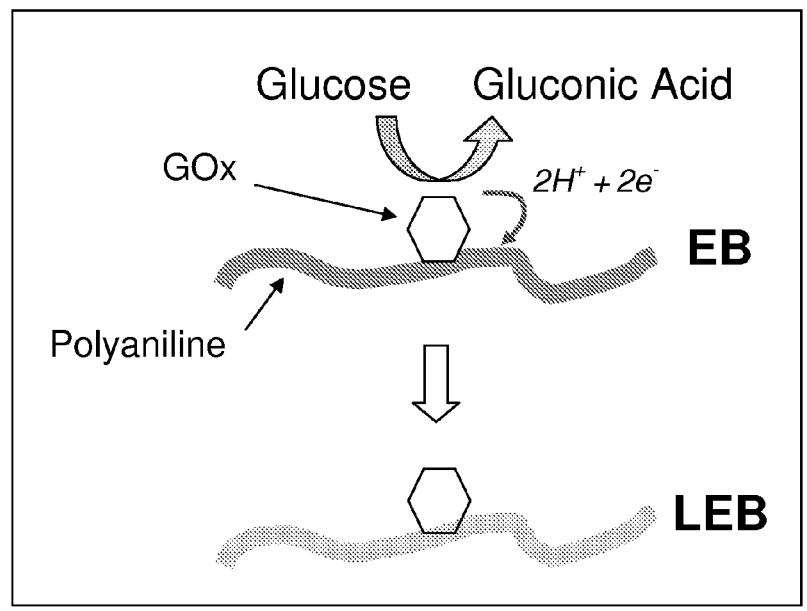
FIG. 5 is a schematic illustration of reduction of polyaniline from EB (blue in color) to LEB (yellow in color) by glucose.

This reaction is also represented schematically in FIG. 5, where there is a reduction from EB (blue in color) to LEB (yellow in color) by glucose.

The rate of this reaction depends of the glucose concentration, as well as other factors including body temperature and the presence of interferants such as ascorbic acid. Under physiological conditions, LEB is unstable and would be quickly reoxidized by dissolved oxygen or other ambient species, so the polymer would constantly be regenerating. This is significant because previous efforts by others to fabricate polyaniline-based optical glucose sensors were often intended for ex-vivo operation only and the sensing element had to be regenerated or discarded after each use.

EXAMPLES

Example I

Glucose oxidase was used as a sensitizing agent to alter the oxidation state of polyaniline in the presence of glucose. This was detected by measuring the change in the absorbance spectrum over time:

A 0.1 mg sample of EB was dissolved in 4 mL NMP and mixed with 4 mg GOx in a quartz spectrometer cuvette. 4 mg of glucose (1 mg/mL=100 milligrams per deciliter) was added to match normal physiological conditions, which should be in the range of approximately 80 to 120 mg/dL. Absorbance spectra taken every two minutes clearly showed the peak reduction at 635 nm characteristic of reduction from EB towards LEB.

Figure 6:
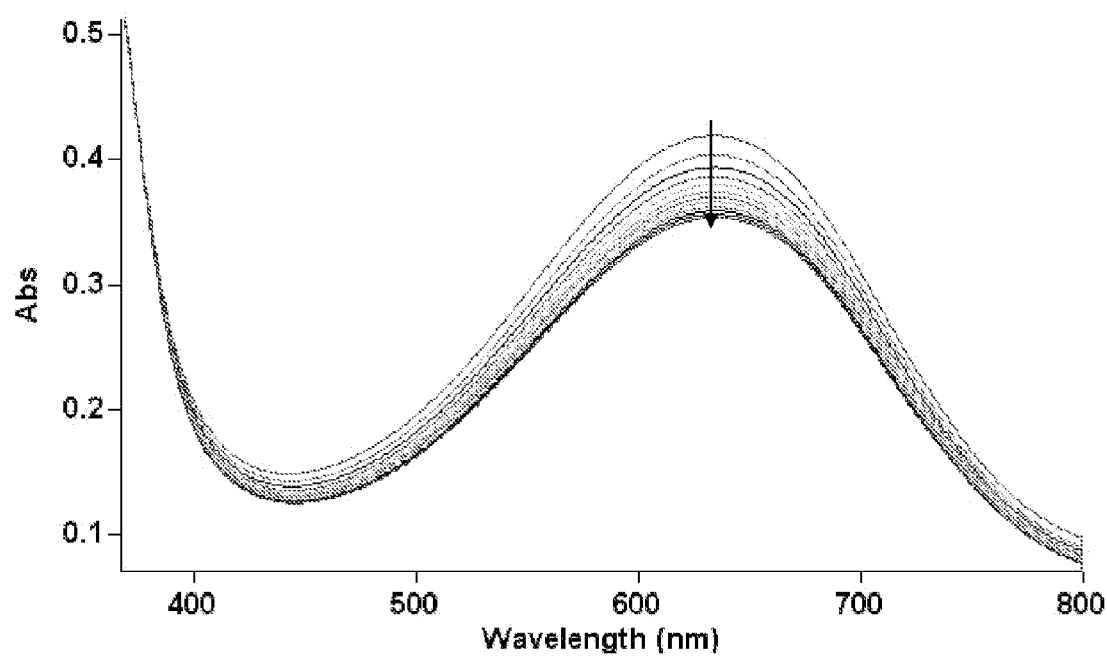
FIG. 6 is a graph showing the absorbance spectra at 2 minute intervals of EB in NMP being reduced towards LEB by glucose in the presence of GOx.

FIG. 6 shows the absorbance spectra at 2 minute intervals of EB in NMP being reduced towards LEB by glucose in the presence of GOx.

Figure 7:
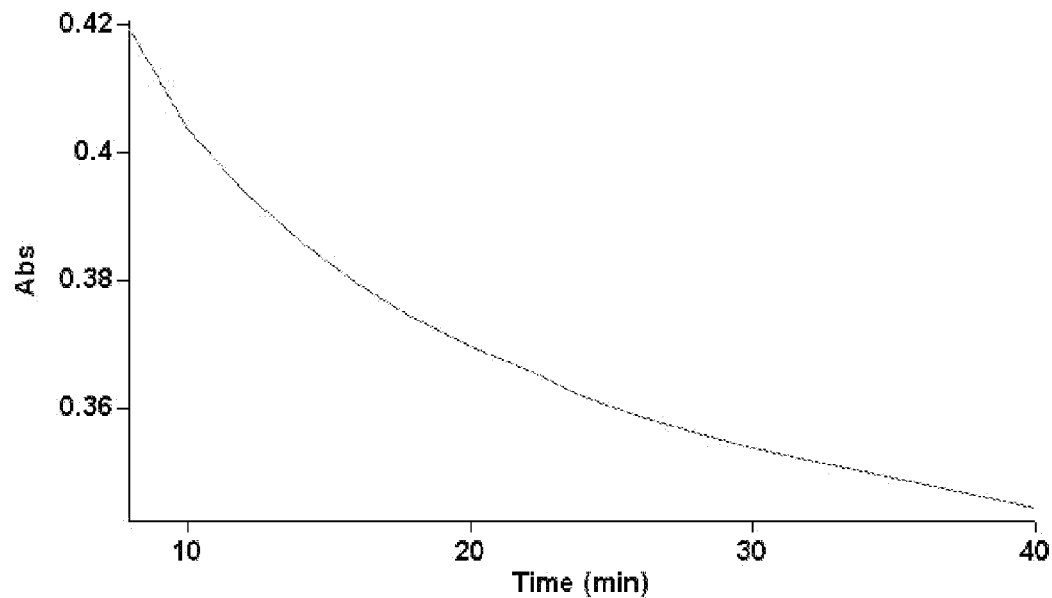
FIG. 7 is a graph showing the change in absorbance at 635 nm over time.

Kinetics analysis shows that the absorbance at 635 nm follows a first-order exponential decay function. FIG. 7 shows the change in absorbance at 635 nm over time.

Although the response time appears to be slow in this example, the reaction speed can be increased in the actual device. The enzyme can be present in higher concentrations and in close contact with the thin film and/or fiber network polymer matrix. Additionally, polyaniline material can be made with a nanofiber morphology so that the polyaniline materials have a very high surface area per volume and can immobilize and confine the enzyme, leading to an additional potential increase in enzymatic activity.

Figure 8:
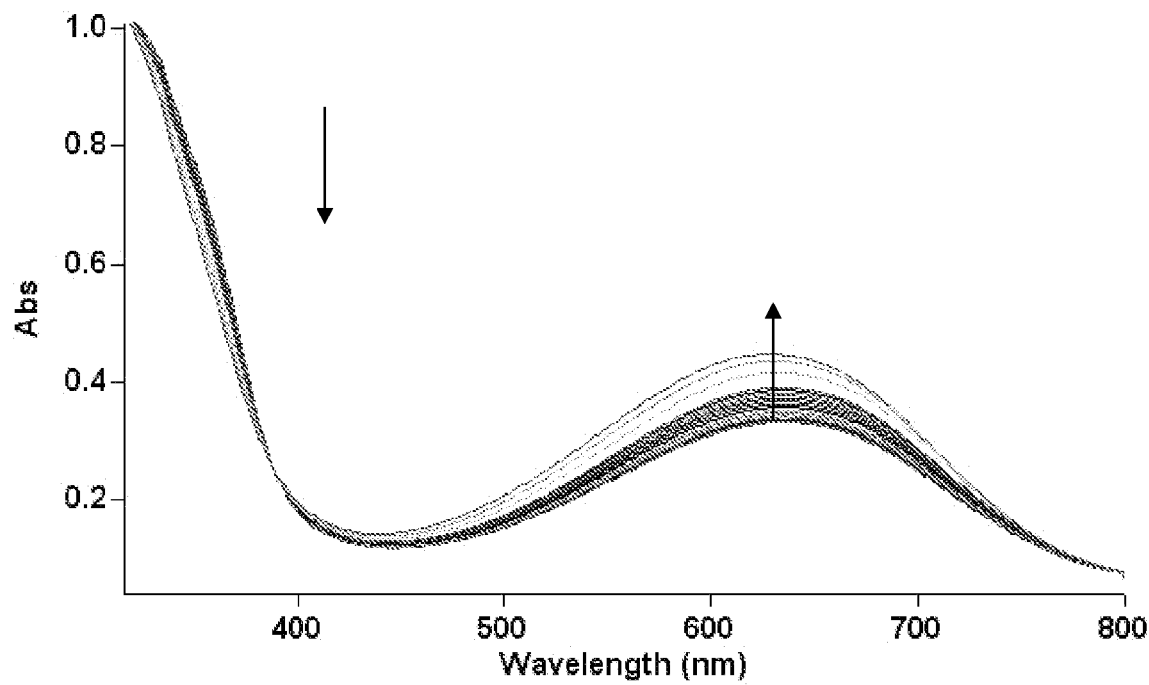
FIG. 8 is a graph showing the partially reduced polymer is reoxidized by the dissolved ambient oxygen with spectra taken at 2 min intervals. Note the isosbestic point at 390 nm, which indicates that no other species were produced.
Figure 9:
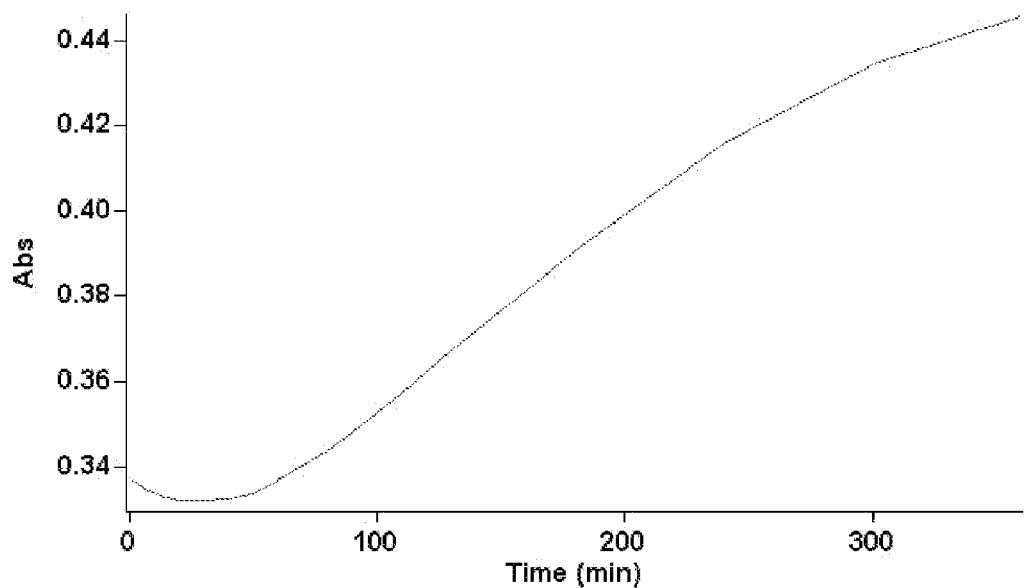
FIG. 9 is a graph showing the absorbance at 635 during the reoxidation phase.

After the glucose is consumed, the polyaniline in the NMP solution in the partially reduced leucoemeraldine form is reoxidized by the dissolved oxygen that originates from the ambient atmosphere, as shown in FIGS. 8 and 9: FIG. 8 shows the partially oxidized polymer is reoxidized by the dissolved ambient oxygen with spectra taken at 2 min intervals. Note the isosbestic point at 390 nm, which indicates that no other species were produced. FIG. 9 shows the absorbance at 635 during the reoxidation phase.

Example II

Figure 10:
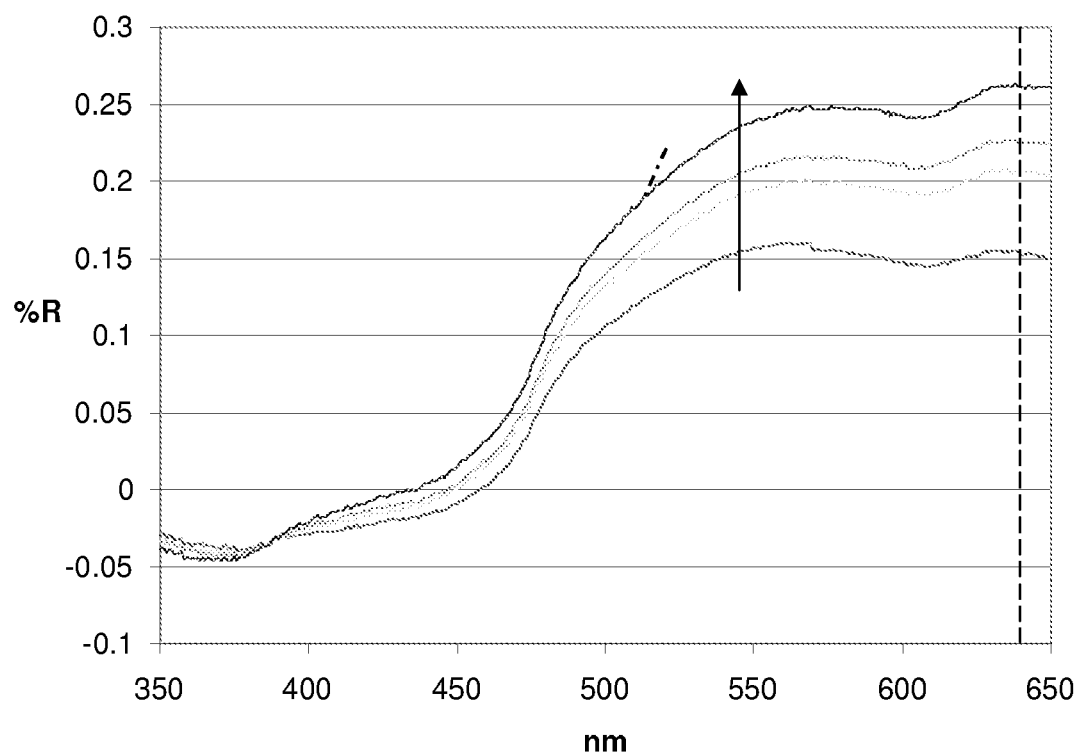
FIG. 10 is a graph showing the modulated specular reflectance of a substrate/thin film over time as the oxidation state of the polymer changes, becoming more reduced.

As an in vitro demonstration of the biosensor method, a prototype was constructed and tested as follows:

A thin film of EB was drop-cast from a 4 mg/mL NMP solution onto a glass slide and allowed to dry. This slide was placed in front of a reflective substrate inside a photometric cuvette filled with a phosphate buffer solution (PBS) used to simulate interstitial fluid. This cuvette was inserted into a UV-VIS spectrophotometer set to measure the specular reflectance of the substrate/thin film system in the wavelength range of 350-650 nm. Ascorbic acid, a reducing agent, was added to the PBS and the change in specular reflectance was recorded in two minute intervals. The results are displayed in FIG. 10, which demonstrates how the light absorbance of the EB film modulates the total specular reflectance of the system. Specifically, the dynamic optical signal increases the fastest around 630 nm (dashed line), where the absorbance by the polymer is most markedly decreased as the EB is reduced to LEB, while the signal remains nearly constant around 390 nm, a wavelength at which EB and LEB absorb similarly.

Figure 11:
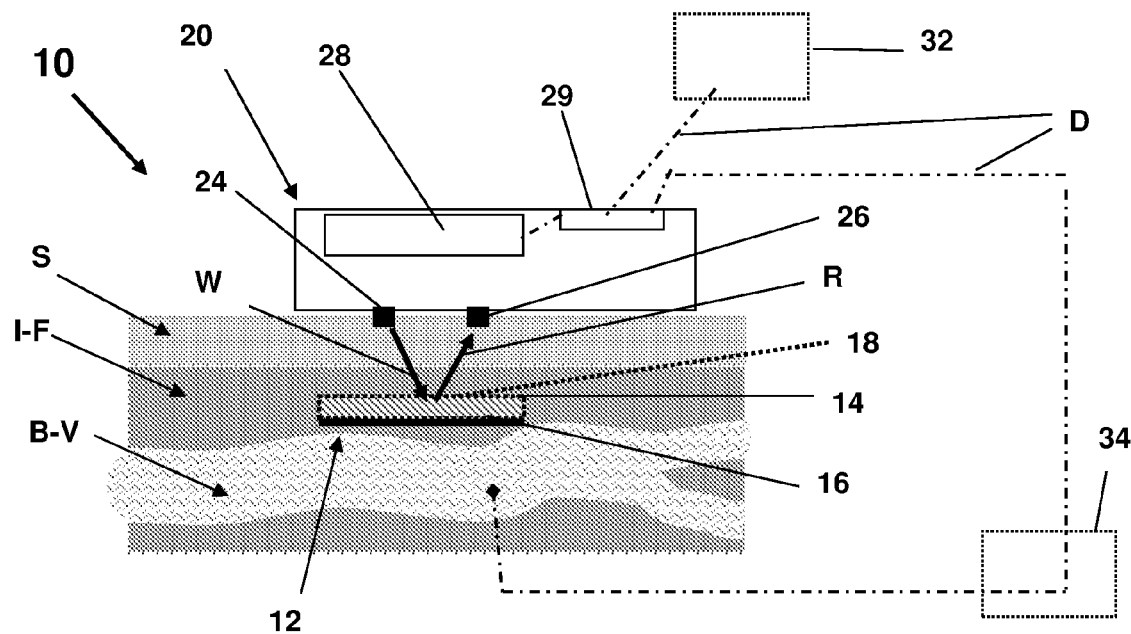
FIG. 11 is a schematic illustration of a biosensor device in situ.

FIG. 11 is a schematic illustration of a suitable in situ biosensor system 10 that includes an implant member 12 and a reader member 20. The schematic illustration in FIG. 11 shows the implant member 12 subcutaneously positioned under a patient's skin S and in contact with the patient's interstitial fluid I-F. In certain preferred embodiments, the implant member 12 is not within or in contact with the patient's blood vessel B-V.

In the schematic illustration, the implant member 12 includes a thin film and/or fiber network material 14 on a reflective substrate 16. The thin film and/or fiber network material 14 includes the polymer component and the sensitizing agent component. In one particular embodiment, the reflective substrate 16 is coated with a thin film and/or fiber network of polyaniline (or other pH sensitive) polymer and immobilized enzyme (or other sensing agent), such as GOx.

The sensitizing agent component can be immobilized or covalently bonded onto the film and/or fiber network material 14. In certain non-limiting examples, covalent bonding can be accomplished by electropolymerizion or graft copolymerization. Since the implant member 12 is in contact with the interstitial fluid I-F, where the concentration of many analytes, including glucose, is proportional to that of the bloodstream, changes in the polymer's oxidation state can be correlated to the analyte concentration in the blood.

The reader member 20 includes one or more light sources 24, such as light emitting diodes (LEDs) on the first side 22 of the reader member 20. The light source diode 24 is in contact with the patient's skin S and emits light of one or more specific diagnostic wavelengths W. The specific diagnostic wavelengths W are chosen to be strongly correlated with changes in the absorbance spectrum of the polymer due to alterations of its oxidation state, onto a subcutaneous implant.

The reader member 20 also includes one or more detectors 26, such as photodiodes, which act as light-detectors to measure the intensity of a reflected light R not absorbed by the film and/or fiber network material 14.

In one embodiment, the reader member 20 may be worn in a manner similar to the wearing of a wristwatch such that at least a first surface 22 of the reader is adjacent to the patient's skin S.

The reader member 20 can also include a suitable data system 29 that calculates the analyte concentration based on preset reaction kinetics equations. The data system 29 can generate real-time data D that can be output to one or more of an attached display 28, an external computer 32, and/or treatment dispenser such as an insulin pump 34.

The light W emitted from the light source 24 shines through the skin S and is incident on the reflective substrate 16. Light that is not absorbed by the polymer component is reflected by the reflective surface 16 as reflected light R.

The reflected light R is measured by one or more photodiodes 32 on the reader member 20. The calculated analyte (e.g. glucose concentration) is displayed on the read-out display 28. It is to be understood that display 28 can be a digital or other suitable display that may also be capable of providing a visual and/or audible signal when certain threshold limits are reached or exceeded.

In certain embodiments, in order to control for variations in the reflected light R due to absorption and scattering by the skin S, the biosensor system 10 can utilize additional light beams to serve as references.

For example, in a first detection system, unmodified polyaniline is coupled with an enzyme as the sensitizing agent and the diode 24 generates a test beam signal at 635 nm (i.e., where the absorption changes the most between the half-oxidized (EB) and reduced (LEB) forms), while a reference beam signal is set at 390 nm (i.e., where the two forms absorb almost identically). By taking a ratio of the two signals, interference by general skin opacity can be lessened.

In a second detection system, a reference beam signal is focused on an enzyme-free region of the film and/or fiber network material in order to help distinguish changes due to common interferants (such as, for example, ascorbic acid). These common interferant substances, unlike glucose, would reduce even the enzyme-free areas.

Figure 12:
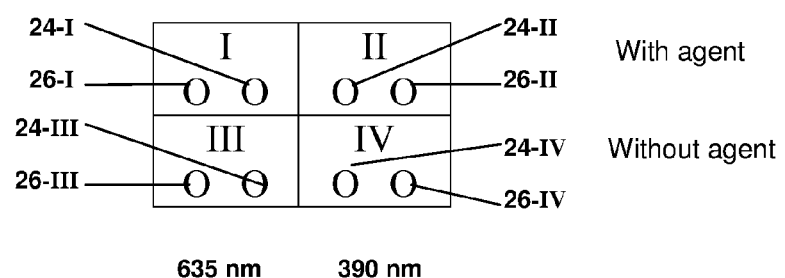
FIG. 12 is a schematic top view of the implant showing the division into sections.

Referring now to FIG. 12, there is shown a schematic illustration of one embodiment of the implant member 12 that can be used in the first and second detection systems described above. FIG. 12 shows a top plan view of the implant member 12 having a "4-quadrant" configuration. It is to be understood, however, that the implant member 12 can have other configurations and/or be divided into fewer or greater sections, and that the term "quadrant" is used herein for ease of explanation.

In the use of an embodiment having the implant member 12 shown in FIG. 12, it is to be understood that the reader member 20 can have multiple light sources 24 and multiple light detectors 26. In such embodiment, each section I-IV can be probed by its own light source 24-I, 24-II, 24-III and 24-IV and reflected light from each section I-IV can be received by its own detector 26-I, 26-II, 26-III and 26-IV within the reader member 20. Again, it is to be understood that; in other embodiments, reader member 20 can have one light source 24 that can alternately probe different sections with light W, and/or have one detector 26 that sequentially receives reflected light R from the alternately probed sections.

The reader member 20 measures how particular ratios of the reflected light R from the sections I-IV change over time and calculates the corresponding analyte concentration. For example, the ratio I/II would remain constant in the absence of analyte, but increase over time when the analyte was present as the polymer would become reduced. In an embodiment where the polymer comprises polyaniline, decreasing the absorbance at 635 nm thus allows more light of that color to be reflected by the reflective substrate 16. For example, interferants, such as ascorbic acid, that reduce the polymer would affect all of the sections equally.

In certain embodiments, the reflective substrate 16 and/or polymer:sensitizing agent film and/or fiber network material 14 may also be patterned in order to improve the signal-to-noise ratio. The patterning can thus increase the reflection by the desired light wavelengths and reduce the interference by other wavelengths. Each section can be specially patterned to reduce "cross-talk." In addition, the polymer:sensitizing agent film and/or fiber network material 14 thicknesses can also be optimized for each section so that undesired wavelengths won't be reflected as strongly. The substrate may be patterned to enable the use of a single light source to monitor two or more portions of the array that incorporate different sensitizing agents, through, for example, formulating substrates such that the light reflected from polymer regions incorporating different sensitizing agents reflect light of different optical polarizations. In this case, the optical detector would be modified to distinguish the polarization of the reflected light.

In certain embodiments, the reader member 20 probes the implant member with light in the spectral region of about 630-650 nm. Also, the reader member 20 can emit light in the spectral region of about 380-400 nm to calibrate the biosensor system 10.

Also, in certain embodiments, the implant member 12 can have a suitable coating 18 that keeps interferants from interacting with the sensitizing agent, as well as preventing damage due to the subject's immune response.

In another aspect, there is provided a biosensor system 10 that can be used to monitor more that one type of analyte, including measuring more than one type of analyte with the same biosensor system. The biosensor system can be adapted to sense a wide variety of biological analytes. In one non-limiting example, the biosensor system can use a suitable sensitizing agent that catalyzes an oxidation-reduction reaction in the presence of the desired target molecule. One class of suitable sensitizing agents includes enzymes classified as an "alcohol oxidoreductase" and use $O_2$ as its natural electron acceptor. These are identified by possessing an Enzyme Commission (EC) number of the form (1.1.3.x), and are listed in table 1 (below). GOx is a member of this group (EC number 1.1.3.4), and some other notable examples include cholesterol oxidase (1.1.3.6) and alcohol oxidase (1.1.3.13), which would detect their respective substrates in a very similar fashion to GOx if coupled with the polymer in the implant.

Alcohol oxidoreductase enzymes are characterized by the ability to catalyze an oxidation-reduction reaction involving one or more alcohol (—OH) functional groups in a specific substrate or group of substrates. If "X" indicates the name of a particular substrate, then the associated enzyme is called "X oxidase." Under normal conditions, if $O_2$ is the electron acceptor, the enzyme catalyzes a reaction of the following form:

$$X + O_2 \rightarrow \text{Oxidized } X + H_2O_2$$

In the sensing device, however, the polymer itself acts as the electron and/or proton acceptor in the place of molecular oxygen. Then the enzyme catalyzed reaction is:

$$X + \text{Oxidized Polymer} \rightarrow \text{Oxidized } X + \text{Reduced Polymer}$$

Here the designations "Oxidized Polymer" or "Reduced Polymer" are relative terms which may refer to a broad range of intermediate oxidation states. When the analyte levels drop, the polymer is regenerated over time by dissolved $O_2$ and/or other oxidizing species in the body tissues.

TABLE 1

| | |
|---|---|
| 1.1.3.3 | Malate oxidase |
| 1.1.3.5 | Hexose oxidase |
| 1.1.3.4 | Glucose oxidase |
| 1.1.3.6 | Cholesterol oxidase |
| 1.1.3.7 | Aryl-alcohol oxidase |
| 1.1.3.8 | L-gulonolactone oxidase |
| 1.1.3.9 | Galactose oxidase |
| 1.1.3.10 | Pyranose oxidase |
| 1.1.3.11 | L-sorbose oxidase |
| 1.1.3.12 | Pyridoxine 4-oxidase |
| 1.1.3.13 | Alcohol oxidase |
| 1.1.3.14 | Catechol oxidase |
| 1.1.3.15 | (S)-2-hydroxy-acid oxidase |
| 1.1.3.16 | Ecdysone oxidase |
| 1.1.3.17 | Choline oxidase |
| 1.1.3.18 | Secondary-alcohol oxidase |
| 1.1.3.19 | 4-hydroxymandelate oxidase |
| 1.1.3.20 | Long-chain-alcohol oxidase |
| 1.1.3.21 | Glycerol-3-phosphate oxidase |
| 1.1.3.23 | Thiamine oxidase |
| 1.1.3.27 | Hydroxyphytanate oxidase |
| 1.1.3.28 | Nucleoside oxidase |
| 1.1.3.29 | N-acylhexosamine oxidase |
| 1.1.3.30 | Polyvinyl-alcohol oxidase |
| 1.1.3.37 | D-arabinono-1,4-lactone oxidase |
| 1.1.3.38 | Vanillyl-alcohol oxidase |
| 1.1.3.39 | Nucleoside oxidase ($H_2O_2$-forming) |
| 1.1.3.40 | D-mannitol oxidase |
| 1.1.3.41 | Xylitol oxidase |

Analytes may be detected and monitored by this system for in vivo biosensing based on the optical response of electronic polymers through the use of electronic polymers that contain other pH sensitive groups, for example, but not limited to, pyridine and/or pyrazine containing polymers that also change absorption range with change in local pH. The sensitivity of the optical response of these polymers to a broader range of analytes can be achieved through incorporation of other sensitizing agents that can cleave protons from target analytes.

Specific examples include the following non-limiting biosensor systems:

the analyte molecule is glucose, and the sensitizing agent comprises glucose oxidase (GOx);

the analyte molecule is cholesterol, and the sensitizing agent comprises cholesterol oxidase;

the analyte molecule is a primary alcohol, such as ethanol, and the sensitizing agent comprises alcohol oxidase;

the electronic polymer incorporates segments of polyaniline that have repeat lengths of a least four aniline rings;

the electronic polymer comprises an oligomer of aniline incorporating a minimum of four aniline rings;

the electronic polymer incorporates pendent groups comprised of aniline oligomer that has repeat lengths of a least four aniline rings;

the electronic polymer incorporates segments of polypyridine that have repeat lengths of a least four pyridine rings;

the electronic polymer incorporates segments of polypyrazine that have repeat lengths of a least four pyrazine rings;

the electronic polymer comprises an oligomer of pyridine incorporating a minimum of four pyridine rings;

the electronic polymer comprises an oligomer of pyrazine incorporating a minimum of four pyrazine rings;

the electronic polymer incorporates pendent groups comprised of pyridine oligomer that has repeat lengths of a least four pyridine rings; and the electronic polymer incorporates pendent groups comprised of pyrazine oligomer that has repeat lengths of a least four pyrazine rings.

The biosensor system described herein provides an advantageous system for a continuous in vivo sensing of an analyte to be measured. The biosensor system is based on the optical detection of the oxidation state of polyaniline, polypiridine, or polypyrazine, or polymers incorporating oligomers of at least 4 rings of aniline, pyridine, or pyrazine within the main chain or as pendant groups, or their derivatives. Due to its less invasive design and real-time functionality, the biosensor system can be used as a supplement or replacement for currently used glucose monitoring technologies, as well as for monitoring technologies relating to a wide range of other analytes.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

We claim:

1. A system for in vivo biosensing of one or more target analyte molecules in a subject, the system comprising:

at least one implant member configured to be completely implanted in the subject's body and to be exposed to the one or more target analyte molecules in the subject's body, the implant member including a reflective substrate having deposited thereon at least one biocompatible polymer comprised of at least one polyaniline or oligomer thereof, and at least one sensitizing agent; the sensitizing agent configured to cause an oxidation-reduction reaction with the polymer in the presence of the target analyte molecule; the biocompatible polymer configured to immobilize the sensitizing agent without covalent bonding and to accept electrons sufficient to alter the biocompatible polymer's optical properties and to provide a detectable signal;

at least one reader member separate from the implant member and configured to be at least temporarily positioned external to the subjects' body and adjacent to the implant member, the reader member being configured: i) to emit light having one or more specific wavelengths, and ii) to detect a reflected signal from the implant member; and at least one data system configured to determine a concentration of the target analyte molecule.

2. The biosensor system of claim 1, wherein the reader system is configured to substantially continuously detect the reflected signal from the implant member.

3. The biosensor system of claim 1, wherein the polymer is present as a thin film and/or fiber network material on the reflective substrate.

4. The biosensor system of claim 1, wherein the polymer is an electronic polymer having an optical absorption spectrum in the ultraviolet-visible-near infrared (UV-VIS-NIR) range that is dependent on the polymer's oxidation state.

5. The biosensor system of claim 1, wherein the sensitizing agent comprises one or more enzymes.

6. The biosensor system of claim 1, wherein the sensitizing agent comprises an oxidoreductase and the analyte is the associated substrate.

7. The biosensor system of claim 1, wherein the analyte molecule is glucose, and the sensitizing agent comprises glucose oxidase (GOx).

8. The biosensor system of claim 1, wherein the analyte molecule is cholesterol, and the sensitizing agent comprises cholesterol oxidase.

9. The biosensor system of claim 1, wherein the analyte molecule is ethanol, and the sensitizing agent comprises alcohol oxidase.

10. The biosensor system of claim 1, wherein the polymer incorporates segments of polyaniline that have repeat lengths of at least four aniline rings, or oligomers thereof.

11. The biosensor system of claim 4, wherein the electronic polymer incorporates pendent groups comprised of aniline that has repeat lengths of at least four aniline rings, or oligomers thereof.

12. The biosensor system of claim 1, wherein the polymer incorporates segments of pyridine that have repeat lengths of at least four pyridine rings, or oligomers thereof.

13. The biosensor system of claim 1, wherein the polymer incorporates segments of pyrazine that have repeat lengths of at least four pyrazine rings, or oligomers thereof.

14. The biosensor system of claim 1, wherein the polymer incorporates pendent groups comprised of pyridine oligomer that has repeat lengths of at least four pyridine rings, or oligomers thereof.

15. The biosensor system of claim 1, wherein the polymer incorporates pendent groups comprised of pyrzine oligomer that has repeat lengths of at least four pyrazine rings, or oligomers thereof.

16. The biosensor system of claim 1, wherein the reader member is configured:

i) to focus a reference beam signal on a region of the implant member that is free of the sensitizing agent, and ii) to distinguish changes due to the presence of interferants in the interstitial fluid in the subject.

17. The biosensor system of claim 1, wherein the implant member includes a plurality of sections, each section being configured to show how ratios of the reflected light from each section change over time and to determine the corresponding analyte concentration.

18. The biosensor system of claim 17, wherein the reader member includes at least one light source and at least one detector associated with each section,
whereby each light source is configured to send light to each section, and whereby each detector is configured to receive light from each section.

19. The biosensor system of claim 18, wherein the implant member further includes a coating that is optimized for each section so that undesired wavelengths are not reflected as strongly as desired wavelengths.

20. The biosensor system of claim 1, wherein the implant member further includes a coating configured to keep interferants from interacting with the implant member.

21. The biosensor system of claim 1, wherein the implant member further includes a coating configured to prevent damage due to the subject's immune response.

22. The biosensor system of claim 1, wherein the sensitizing agent comprises one or more of:
malate oxidase, hexose oxidase, glucose oxidase, cholesterol oxidase, aryl-alcohol oxidase, L-gulonolactone oxidase, galactose oxidase, pyranose oxidase, L-sorbose oxidase, pyridoxine 4-oxidase, alcohol oxidase, catechol oxidase, (S)-2-hydroxy-acid oxidase, ecdysone oxidase, choline oxidase, secondary-alcohol oxidase, 4-hydroxymandelate oxidase, long-chain-alcohol oxidase, glycerol-3-phosphate oxidase, thiamine oxidase, hydroxyphytanate oxidase, nucleoside oxidase, N-acylhexosamine oxidase, polyvinyl-alcohol oxidase, D-arabinono-1,4-lactone oxidase, vanillyl-alcohol oxidase, nucleoside oxidase, D-mannitol oxidase, and xylitol oxidase.

23. A method for in vivo biosensing of specific analyte molecule concentrations in a subject, comprising:
a) completely implanting at least one implant member in the subject's body wherein the implant member is exposed to specific analyte molecule concentrations in the subject,
the implant including a reflective substrate having deposited thereon at least one biocompatible polymer comprised of at least one polyaniline or oligomer thereof, and at least one sensitizing agent that causes an oxidation-reduction reaction with the polymer in the presence of the target analyte molecule the biocompatible polymer configured to immobilize the sensitizing agent without covalent bonding and to accept electrons sufficient to alter the biocompatible polymer's optical properties and to provide a detectable signal;
b) at least temporarily positioning a reader member external to the subjects' body and adjacent to the implant member, the reader member emitting light of specific wavelengths and detecting a reflected signal from the implant member; and
c) determining a concentration of the target analyte molecule from the reflected signal.

24. The method of claim 23, further including emitting with multiple beams of light of specific wavelengths and detecting reflected signals from the implant member.

25. The method of claim 23, wherein the reader member focuses a reference beam signal on a region of the implant member that is free of the sensitizing agent, and distinguishes changes due to the presence of interferants in the interstitial fluid in the subject.

26. The method of claim 23, wherein the implant member includes a plurality of sections, each section being configured to show how ratios of the reflected light from each section change over time and to determine the corresponding analyte concentration.

27. The method of claim 23, wherein the reader member includes at least one light source and at least one detector associated with each section, whereby each light source sends light to each section, and whereby each detector receives light from each section.

28. The method of claim 23, wherein the polymer comprises an electronic polymer.

29. The method of claim 23, wherein the polymer is an electronic polymer having an optical absorption spectrum in the ultraviolet-visible-near infrared range that is dependent on the polymer's oxidation state.

30. The method of claim 23, wherein the polymer comprises one or more of:
the polymer incorporates segments of polyaniline that have repeat lengths of at least four aniline rings, or oligomers thereof;
the polymer comprises an oligomer of aniline incorporating a minimum of four aniline rings;
the polymer incorporates pendent groups comprised of polyaniline oligomer that has repeat lengths of at least four aniline rings, or oligomers thereof;
the polymer incorporates segments of pyridine that have repeat lengths of at least four pyridine rings, or oligomers thereof;
the polymer incorporates segments of pyrazine that have repeat lengths of at least four pyrazine rings, or oligomers thereof;
the polymer comprises an oligomer of pyridine incorporating a minimum of four pyridine rings;
the polymer comprises an oligomer of pyrazine incorporating a minimum of four pyrazine rings;
the polymer incorporates pendent groups comprised of pyridine oligomer that has repeat lengths of at least four pyridine rings, or oligomers thereof; and
the polymer incorporates pendent groups comprised of pyrzine oligomer that has repeat lengths of at least four pyrazine rings, or oligomers.

31. The method of claim 23, wherein the analyte molecule is glucose, and the sensitizing agent comprises glucose oxidase (GOx).

* * * * *